US008183270B2

(12) United States Patent
Loso et al.

(10) Patent No.: US 8,183,270 B2
(45) Date of Patent: *May 22, 2012

(54) INSECTICIDAL N-SUBSTITUTED (2-SUBSTITUTED-1,3-THIAZOL)ALKYL SULFOXIMINES

(75) Inventors: Michael R. Loso, Carmel, IN (US); Benjamin M. Nugent, Brownsburg, IN (US); Yuanming Zhu, Carmel, IN (US); Thomas L. Siddall, Zionsville, IN (US); Francis E. Tisdell, Carmel, IN (US); Jim X. Huang, Carmel, IN (US); Zoltan L. Benko, Indianapolis, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/948,886

(22) Filed: Nov. 18, 2010

(65) Prior Publication Data
US 2011/0060018 A1 Mar. 10, 2011

Related U.S. Application Data

(62) Division of application No. 11/897,510, filed on Aug. 30, 2007, now Pat. No. 7,863,303.

(60) Provisional application No. 60/841,938, filed on Sep. 1, 2006.

(51) Int. Cl.
*A01N 43/78* (2006.01)
*C07D 277/30* (2006.01)
*C07D 417/06* (2006.01)
*A61P 7/04* (2006.01)

(52) U.S. Cl. ........................ 514/365; 548/205
(58) Field of Classification Search .................. None
See application file for complete search history.

(56) References Cited

U.S. PATENT DOCUMENTS

| | | | |
|---|---|---|---|
| 3,711,486 A | 1/1973 | Torba et al. | |
| 3,787,420 A | 1/1974 | Torba et al. | |
| 3,852,279 A | 12/1974 | Krapcho et al. | |
| 4,577,028 A | 3/1986 | Martin et al. | |
| 4,692,184 A | 9/1987 | Lee | |
| 4,747,871 A | 5/1988 | Ruminski et al. | |
| 4,833,158 A | 5/1989 | Twydell et al. | |
| 4,948,896 A | 8/1990 | Nagao | |
| 4,973,695 A | 11/1990 | Yamashita et al. | |
| 5,053,516 A | 10/1991 | Hartmann et al. | |
| 5,099,023 A | 3/1992 | Miller et al. | |
| 5,099,024 A | 3/1992 | Pulwer et al. | |
| 5,118,809 A | 6/1992 | Cevasco et al. | |
| 5,124,458 A | 6/1992 | Cevasco et al. | |
| 5,169,432 A | 12/1992 | Auinbauh et al. | |
| 5,225,560 A | 7/1993 | Cevasco et al. | |
| 5,227,491 A | 7/1993 | Doehner, Jr. | |
| 5,229,519 A | 7/1993 | Zhang et al. | |
| 6,060,502 A | 5/2000 | Louder et al. | |
| 7,511,149 B2 | 3/2009 | Arndt et al. | |
| 7,541,469 B2 | 6/2009 | Renga et al. | |
| 7,604,815 B2 | 10/2009 | Loso et al. | |
| 7,678,920 B2 | 3/2010 | Zhu et al. | |
| 2003/0078430 A1 | 4/2003 | Satake et al. | |
| 2004/0158067 A1 | 8/2004 | Hutchison et al. | |
| 2006/0199964 A1 | 9/2006 | Jackson et al. | |
| 2007/0203191 A1 | 8/2007 | Loso et al. | |
| 2007/0249837 A1 | 10/2007 | Gebhardt et al. | |
| 2007/0299264 A1 | 12/2007 | Huang et al. | |
| 2008/0108665 A1 | 5/2008 | Huang et al. | |
| 2008/0108666 A1 | 5/2008 | Loso et al. | |
| 2008/0108667 A1 | 5/2008 | Zhu et al. | |
| 2008/0132705 A1 | 6/2008 | Heller et al. | |
| 2008/0194830 A1 | 8/2008 | Meyer et al. | |
| 2008/0280915 A1 | 11/2008 | Loso et al. | |

FOREIGN PATENT DOCUMENTS

| | | |
|---|---|---|
| DE | 19523658 A1 | 6/1995 |
| WO | WO98/02492 | 1/1998 |
| WO | WO01/07430 | 2/2001 |
| WO | PCT/US2007/019176 | 2/2008 |

OTHER PUBLICATIONS

Kagabu, Shinzo and Medej, Somporn; "Stability Comparison of Imidacloprid and Related Compounds under Simulated Sunlight, Hydrolysis Conditions, and to Oxygen;" Biosci. Biotech. Biochem., 59 (6), 980-985, (1995).
Kagabu, Shinzo; Murata, Natsue; Hibino, Rika; Hanzawa, Madoka and Nishimura, Keiichiro; "Insecticidal and Neuroblocking Activities of Thiamethoxam-Type Compounds in the American Cockroach (*Periplaneta americana* L.);" J. Pesticide Sci. 30(2), 111-115 (2005).
Sparks, Thomas C.; Crouse, Gary D. and Durst, Gregory; "Natural products as insecticides: the biology, biochemistry and quantitative structure-activity relationships of spinosyns and spinosoids;" Pest Management Science, 57:896-905 (2001).
Wakita, Takeo; Kinoshita, Katsutoshi; Kodaka, Kenji; Yasui, Naoko; Naoi, Atsuko and Banba, Sinichi; "Synthesis and Structure-Activity Relationships of Dinotefuran Derivatives: Modification in the Tetrahydro-3-furylmethyl Part;" J. Pesticide Sci. 29 (4), 356-363 (2004).
Kollmeyer, Willy D.; Flattum, Roger F.; Foster, James P.; Powell, James E.; Schroeder, Mark E. and Soloway, S. Barney; "Discovery of the Nitromethylene Heterocycle Insecticides;" Nicotinoid Insecticides and the Nicotinic Acetylcholine Receptor [Eds.: Yamamoto, I. and Casida, J.E.]; 1999, pp. 71-89, Springer-Verlag, Tokyo.
Shiga, Yasushi; Okada, Itaru and Fukuchi, Toshiki; "Synthesis and Acaricidal Activity of N-(1,3,4-Thiadiazol-2-yl)cyclopropanecarboxamides;" J. Pesticide Sci. 28, 61-63 (2003).
Singer, Alvin; McElvain, S.M. 2,6-Dimethylpyridine. Organic Syntheses, 1934, 14, 30.
Haibo Yu, Zhenfang Qin, Hong Dai, Xin Zhang, Xue Qin, Tingting Wang and Jianxin Fang, Synthesis and Insecticidal Activity of N-Substituted (1,3-Thiazole)alkyl Sulfoximine Derivatives, J. Agric. Food Chem. 2008, 56, 11356-11360.
Haibo Yu, Zhenfang Qin, Hong Dai, Xin Zhang, Xue Qin, Tingting Wang, and Jianxin Fang, Synthesis and insecticidal activity of N-cyano 2-(substituted amino) ethyl methyl sulfoximine derivatives, General Papers, ARKIVOC 2008 (xvi) 99-109.

(Continued)

*Primary Examiner* — Kamal Saeed
(74) *Attorney, Agent, or Firm* — Carl D. Corvin

(57) ABSTRACT

N-Substituted (2-substituted-1,3-thiazol)alkyl sulfoximines are effective at controlling insects.

3 Claims, No Drawings

OTHER PUBLICATIONS

Kawanshi, Hiroyuki; Morimoto, Hiroshi; Nakano, Takao; Watanabe, Tatsuya; Oda, Kuniyuki; and Tsujihara, Kenji; "Steroselective Synthesis of Antifungal Sulfoximines, Novel Trizaoles II;" Heterocycles, vol. 49, 1998, pp. 181-189.

Reichert, Anja; Frohlich, Roland; Ferguson, Roderick; Kraft, Arno; "Binding Interactions Between 3-aryl-1,2,4-oxadiazol-5-ones and a trisimidazoline base;" J. Chem. Soc., Perkin Trans. 1, 2001, pp. 1321-1328.

Garcia Mancheno, Olga; Bistri, Olivia; and Bolm, Carsten; "Iodinane- and Metal-Free Synthesis of N-Cyano Sulfilimines: Novel and Easy Access of NH-Sulfoximines;" Organic Letters, 2007, vol. 9, No. 19, pp. 3809-3811.

Kiriyama K et al: Insecticidal and neuroblocking activities of acetamiprid and related compounds Journal of Pesticide Sciences, Pesticide Science Society, Tokyo, JP, vol. 28, No. 1, 2003, pp. 80-17.

F Zaragoza Dorwald Side Reactions in Organic Synthesis 2005, Wiley-VCH.

INSECTICIDAL N-SUBSTITUTED (2-SUBSTITUTED-1,3-THIAZOL)ALKYL SULFOXIMINES

CROSS-REFERENCE TO RELATED APPLICATION

This application claims priority from provisional application 60/841,938 filed in the United States Patent Office on Sep. 1, 2006. This application also claims benefit of U.S. non-provisional application Ser. No. 11/897,510 filed 30 Aug. 2007.

BACKGROUND OF THE INVENTION

The present invention concerns novel N-substituted (2-substituted-1,3-thiazol)alkyl sulfoximines and their use in controlling insects, particularly aphids and other sucking insects, as well as certain other invertebrates. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

U.S. Patent Application Publication 2005/0228027 A1 describes certain sulfoximine compounds including some containing (2-chloro-1,3-thiazol)alkyl groups and their use in controlling insects. It will be demonstrated that certain (2-substituted-1,3-thiazol-4-yl)alkyl sulfoximines and (2-substituted-1,3-thiazol-5-yl)alkyl sulfoximines will have comparable or even greatly improved activity.

SUMMARY OF THE INVENTION

This invention concerns compounds useful for the control of insects, especially useful for the control of aphids and other sucking insects. More specifically, the invention concerns compounds of the formula (I)

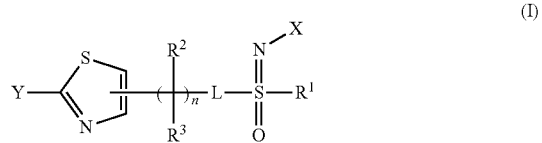

(I)

wherein

X represents $NO_2$, CN, $COOR^4$ or $COR^5$;

L represents either a single bond or $-CH(CH_2)_m-$ where m is an integer from 1-3 in cases where $R^1$, S and L taken together represent a 4-, 5-, or 6-membered ring;

n is an integer from 0-3;

Y represents $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, fluoro, bromo, iodo, $C_1$-$C_4$ alkoxy, $C_1$-$C_4$ haloalkoxy, CN, $NO_2$ or $R^6SO_z$ where z is an integer from 0-2;

$R^1$ represents $C_1$-$C_4$ alkyl, $C_1$-$C_4$ haloalkyl, $C_3$-$C_6$ alkenyl, $C_3$-$C_6$ haloalkenyl, $C_3$-$C_6$ alkynyl, or $-(CH_2)-$ in cases where $R^1$, S and L taken together represent a 4-, 5-, or 6-membered ring;

$R^2$ and $R^3$ independently represent hydrogen, methyl, ethyl, cyclopropyl, fluoro, chloro, bromo, or iodo;

$R^4$ represents $C_1$-$C_4$ alkyl, $C_1$-$C_4$ haloalkyl, aryl, heteroaryl, arylalkyl or heteroarylalkyl;

$R^5$ represents hydrogen, $C_1$-$C_4$ alkyl, $C_1$-$C_4$ haloalkyl, aryl, heteroaryl; arylalkyl or heteroarylalkyl; and $R^6$ represents $C_1$-$C_4$ alkyl, $C_1$-$C_4$ haloalkyl, $C_3$-$C_6$ alkenyl, $C_3$-$C_6$ haloalkenyl or $C_3$-$C_6$ alkynyl.

Preferred compounds of formula (I) include the following classes:

(1) Compounds of formula (I) wherein X is $NO_2$ or CN, most preferably CN.

(2) Compounds of formula (I) wherein Y is $C_1$-$C_4$ haloalkyl, fluoro, or bromo, most preferably $CF_3$.

(3) Compounds of formula (I) wherein n is either 0 or 1 and $R^1$, S and L taken together form a saturated 5-membered ring having the structure

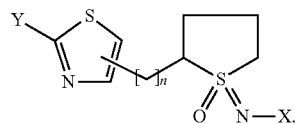

(4) Compounds of formula (I) wherein L represents a single bond and n>0 having the structure

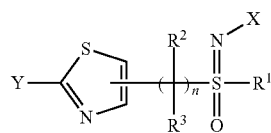

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methylethyl, propyl, 1,1-dimethylethyl, and cyclopropyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo" includes fluorine, chlorine, bromine and iodine, with fluorine being preferred. The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$OC(O)alkyl, $C_1$-$C_6$ NHC(O)alkyl, C(O)OH, $C_1$-$C_6$C(O)Oalkyl, C(O)NH$_2$, $C_1$-$C_6$C(O)NHalkyl, or $C_1$-$C_6$C(O)N(alkyl)$_2$, provided that the substituents are sterically compatible and the rules of chemical bonding and strain energy are satisfied.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (Ia), wherein $R^1$, $R^2$, $R^3$, $R^4$, $R^5$, n, X, and Y are as previously defined and L is a single bond, can be prepared by the methods illustrated in Scheme A:

Scheme A

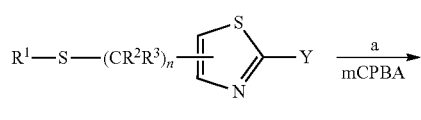

(A)

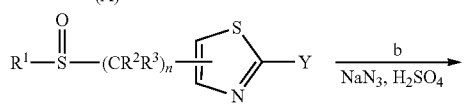

(B)

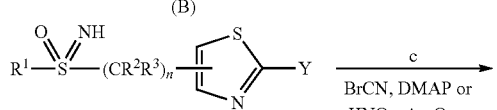

(C)

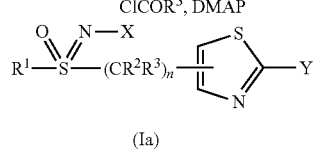

(Ia)

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl ($R^4$) chloroformate in the presence of base such as 4-dimethylaminopyridine (DMAP), or acylated with acyl halide in the presence of base such as 4-dimethylaminopyridine (DMAP) to provide N-substituted sulfoximine (Ia). Base is required for efficient cyanation, carboxylation or acylation and the preferred base is DMAP, whereas sulfuric acid is used as catalyst for efficient nitration reaction.

The compounds of formula (Ia), wherein X represents CN can be prepared by the mild and efficient method illustrated in Scheme B.

Scheme B

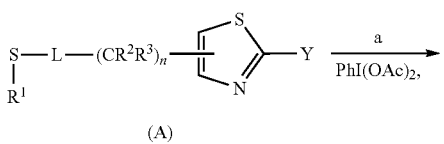

(A)

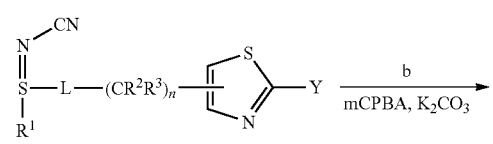

(D)

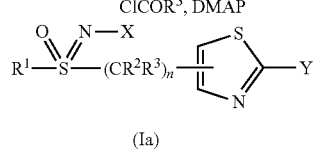

(Ia)

In step a of Scheme B, sulfide is oxidized with iodobenzene diacetate in the presence of cyanamide at 0° C. to give sulfilimine (D). The reaction can be carried out in a polar aprotic solvent like CH$_2$Cl$_2$.

In step b of Scheme B, the sulfilimine (D) is oxidized with mCPBA. A base such as potassium carbonate is employed to neutralize the acidity of mCPBA. Protic polar solvents such as ethanol and water are used to increase the solubility of the sulfilimine starting material and the base employed.

The α-carbon of the N-substituted sulfoximine of formula (Ia), i.e., n=1, $R^3$=H in the (CR$^2$R$^3$) group adjacent to the sulfoximine function can be further alkylated or halogenated in the presence of a base such as potassium hexamethyldisilamide (KHMDS) to give sulfoximines of formula (Ib), wherein $R^1$, $R^2$, X, L and Y are as previously defined and Z is an appropriate leaving group, as depicted in Scheme C. Preferred leaving groups are iodide ($R^6$=alkyl), benzenesulfonimide ($R^6$=F), tetrachloroethene ($R^6$=Cl), and tetrafluoroethene ($R^6$=Br).

Scheme C

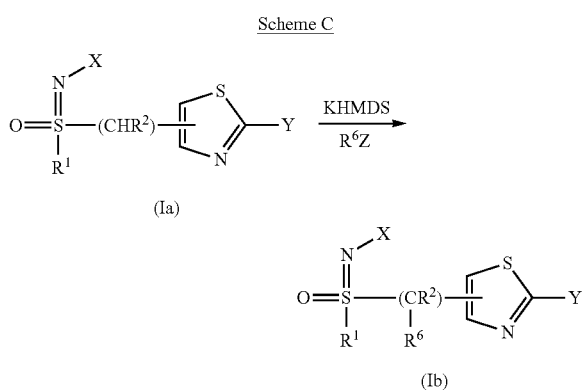

Sulfoximine compounds of formula (Ic) wherein $R^1$, S and L taken together form a saturated 4-, 5- or 6-membered ring and n=1 can be prepared by the methods illustrated in Scheme D wherein X and Y are as previously defined and m is 0, 1, or 2.

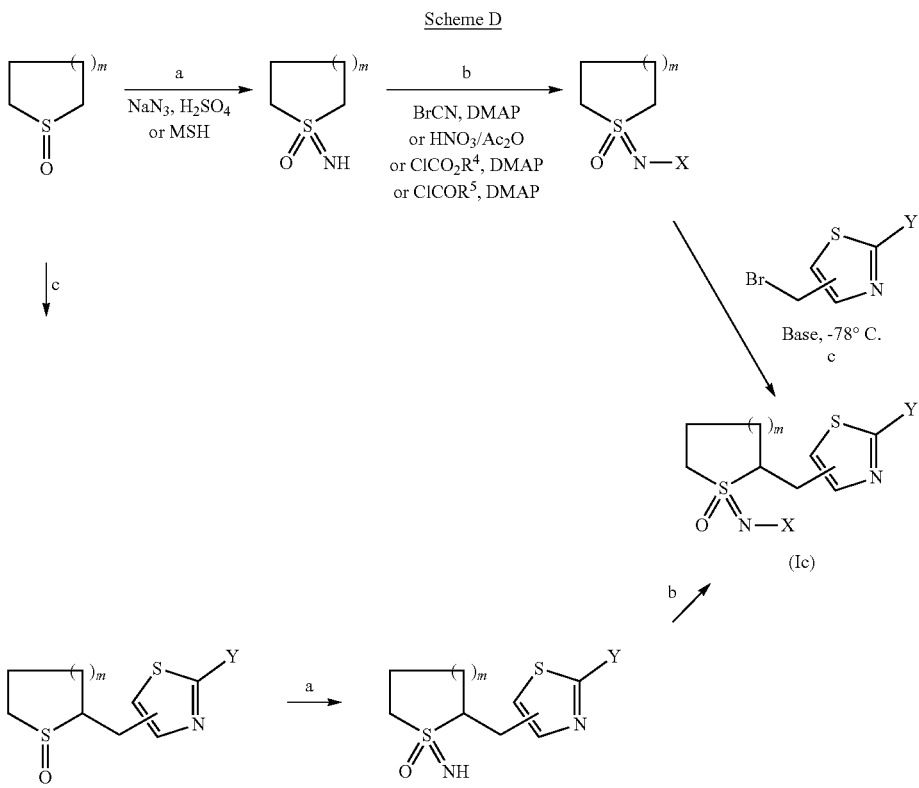

In step a of Scheme D, which is similar to step b of Scheme A, sulfoxide is iminated with sodium azide in the presence of concentrated sulfuric acid or with O-mesitylsulfonylhydroxylamine in a polar aprotic solvent to provide the corresponding N-unsubstituted sulfoximine Chloroform or dichloromethane are the preferred solvents.

In step b of Scheme D, similar to step c of Scheme A, the nitrogen of sulfoximine can be either cyanated with cyanogen bromide, or nitrated with nitric acid followed by treatment with acetic anhydride under refluxing conditions, or carboxylated with methyl chloroformate in the presence of base such as DMAP, or acylated with acyl halide in the presence of base such as 4-dimethylamino-pyridine (DMAP) to provide N-substituted cyclic sulfoximine. Base is required for efficient cyanation, carboxylation or acylation and the preferred base is DMAP, whereas sulfuric acid is used as catalyst for efficient nitration reaction.

In step c of Scheme D, the α-carbon of N-substituted sulfoximine can be alkylated with a 1,3-thiazolyl methyl halide in the presence of a base such as KHMDS or butyl lithium (BuLi) to give the desired N-substituted sulfoximines. The preferred halide can be bromide, chloride or iodide.

Alternatively, the compounds of formula (Ic) can be prepared by a first α-alkylation of sulfoxides to give α-substituted sulfoxides and then an imination of the sulfoxide followed by N-substitution of the resulting sulfoximine by using the steps c, a and b respectively as described above for Scheme D.

The starting sulfides (A) in Scheme A can be prepared in different ways as illustrated in Schemes E, F G, and H.

In Scheme E, the sulfide of formula ($A_1$), wherein $R^1$, $R^2$ and Y are as previously defined, n=1, and $R^3$=H, can be prepared from 1,3-thiazolyl methyl halides of formula (E) by nucleophilic substitution with the sodium salt of an alkyl thiol.

Scheme E

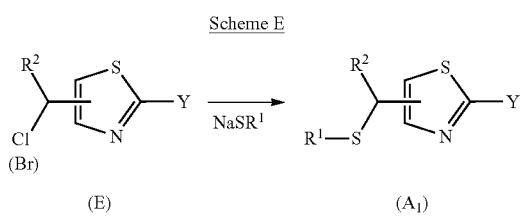

In Scheme F, the sulfide of formula ($A_2$), wherein $R^1$, $R^2$ and Y are as previously defined, n=3, and $R^3$=H, can be prepared from halides of formula (E) by reacting with a 2-mono substituted methyl malonate in the presence of base such as potassium tert-butoxide to provide 2,2-disubstituted malonate, hydrolysis under basic conditions to form a diacid, decarboxylation of the diacid by heating to give a monoacid, reduction of the monoacid with borane-tetrahydrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

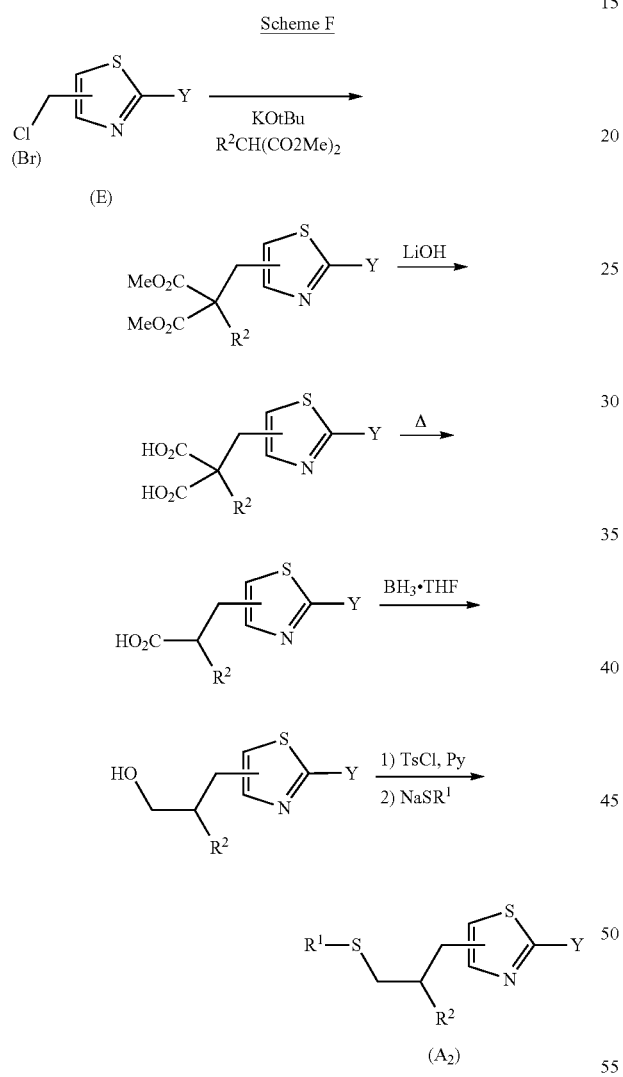

In Scheme G, the sulfide of formula ($A_3$), wherein $R^1$, $R^2$ and Y are as previously defined, n=2, and $R^3$=H, can be prepared from the nitrile of formula (F) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahydrofuran complex to provide an alcohol, tosylation of the alcohol with tosyl chloride in the presence of a base like pyridine to give a tosylate and replacement of the tosylate with the sodium salt of the desired thiol.

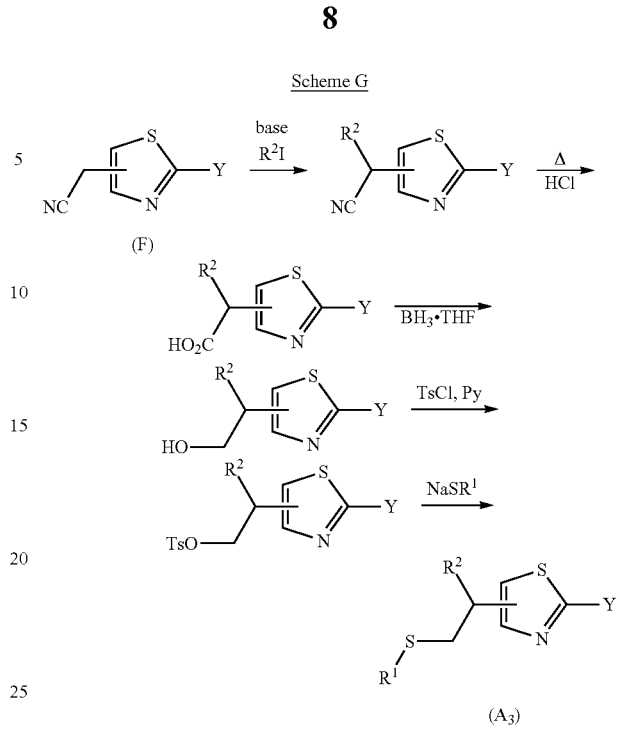

In Scheme H, the sulfide of formula ($A_4$), wherein $R^1$, S and L taken together represents a 4-, 5- or 6-membered ring (m=0, 1, or 2) and n is 0 can be prepared from 1,3-thiazolyl methyl halides (E) by treatment with thiourea, hydrolysis and subsequent alkylation with the appropriate bromo chloroalkane (m=0, 1, or 2) under aqueous base conditions, and cyclization in the presence of a base like potassium-t-butoxide in a polar aprotic solvent such as THF.

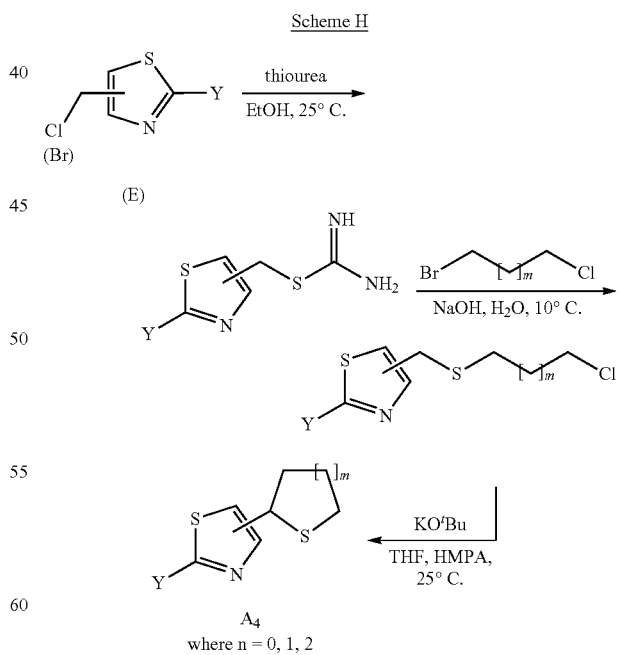

1,3-thiazolyl methyl halides (E) can be prepared according to literature procedures. For example, the preparation of 5-bromomethyl-2-trifluoromethyl-1,3-thiazole ($E_1$) is described in U.S. Pat. No. 5,324,837.

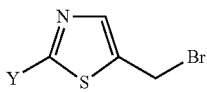

Another procedure, illustrated in Scheme I, is useful for preparing certain 4-chloromethyl 2-substituted-1,3-thiazoles (E$_2$) where Y=C$_1$-C$_4$ (halo)alkyl, or C$_2$-C$_4$ (halo)alkenyl or alkynyl. In this scheme, amides which bear the appropriate Y group are converted to thioamides with phosphorous pentasulfide and then treated ethyl bromopyruvate to provide the corresponding 4-carboethoxy-1,3-thiadiazole (G). Subsequent reduction with lithium aluminum hydride and conversion of the resultant alcohol to the chloride with thionyl chloride provides desired 2-substituted-1,3-thiazol-4-yl methyl chlorides (E$_2$).

Scheme I

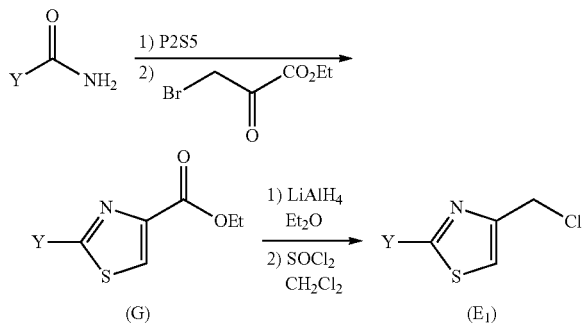

EXAMPLES

These examples are provided to further illustrate this invention. They are not meant to be construed as limiting the invention.

Example I

Methyl(oxido){[2-(trifluoromethyl)-1,3-thiazol-5-yl]methyl}-λ$^4$-sulfanylidenecyanamide (1)

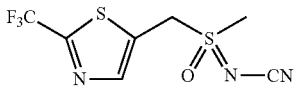

(A)

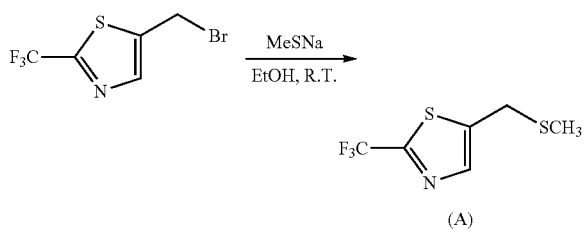

A solution of 5-(bromomethyl)-2-(trifluoromethyl)-1,3-thiazole [prepared in accordance with U.S. Pat. No. 5,338,856] (170 mg, 069 mmol) in 5 mL of ethanol was treated sodium methylthiolate (60 mg, 0.86 mmol) at room temperature. The reaction was complete in 10 min and so the solvent was carefully removed under reduced pressure (40 mmHg) without heating. The residue was partitioned between dichloromethane and dilute hydrochloric acid, washed with saturated brine and dried over sodium sulfate. The solvent was again carefully removed under reduced pressure (40 mmHg) without heating to yield 5-[methylthio)methyl]-2-(trifluoromethyl)-1,3-thiazole (140 mg; 96%) as a pale orange liquid: 1H NMR (CDCl$_3$) δ 7.75 (s, 1H), 3.90 (s, 2H), 2.10 (s, 3H); GCMS (FID) m/z 213 (M+).

(B)

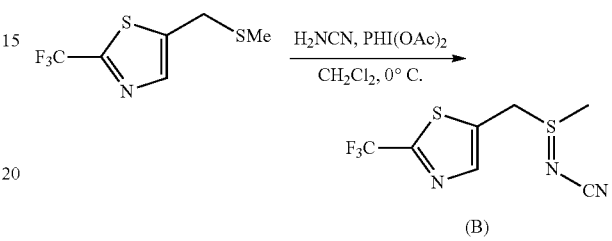

(B)

A solution of 5-[methylthio)methyl]-2-(trifluoromethyl)-1,3-thiazole (140 mg, 0.62 mmol) and cyanamide (35 mg, 0.83 mmol) in 6 mL of dichloromethane was cooled to 0° C. and treated with iodobenzene diacetate (860 mg, 2.59 mmol). A clear yellow solution was obtained. The mixture was allowed to warm to room temperature over an hour and then the solvent removed under reduced pressure and the residue further purified by flash column chromatography on silica gel using a 50% mixture of acetone and petroleum ether as the eluant. The solvents were removed under reduced pressure to yield 130 mg (83%) of (1E)-methyl{[2-(trifluoromethyl)-1,3-thiazol-5-yl]methyl}-λ$^4$-sulfanylidenecyanamide as a pale yellow syrup: 1H NMR (CDCl$_3$) δ 8.00 (s, 1H), 4.60 (s, 2H), 2.85 (s, 3H); LCMS (ESI) m/z 254 (M+H).

(C)

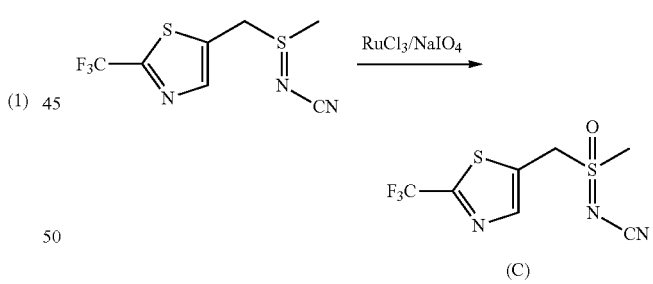

(C)

A rapidly stirring solution of (1E)-methyl[{2-(trifluoromethyl)-1,3-thiazol-5-yl]methyl}-λ$^4$-sulfanylidenecyanamide (86 mg, 0.34 mmol) in 10 mL of dichloromethane was first treated with ruthenium(III) chloride hydrate (8 mg, 0.04 mmol) and then a solution of sodium periodate (146 mg, 0.68 mmol) in 5 mL of water. The dark mixture was stirred for 45 min at room temperature at which point all starting material was consumed. The dark mixture was then passed through a plug of alumina followed by an acetone wash. The combined filtrates were partitioned between dichloromethane and water, washed with brine, and the organic layer dried over sodium sulfate. The solvent was removed under reduced pressure to yield 70 mg (76%) of methyl(oxido){[2-(trifluoromethyl)-1,3-thiazol-5-yl]methyl}-λ$^4$-sulfanylidenecyanamide as a white solid: mp 123-124° C.; 1H NMR (CDCl$_3$) δ 8.00 (s, 1H), 4.95 (s, 2H), 3.10 (s, 3H); LCMS (ESI) m/z 268 (M–H).

Examples II

Methyl(oxido){1-methyl-1-[2-(trifluoromethyl)-1,3-thiazol-5-yl]ethyl}-λ$^4$-sulfanylidenecyanamide (2) and Methyl(oxido){1-[2-(trifluoromethyl)-1,3-thiazol-5-yl]ethyl}-λ$^4$-sulfanylidenecyanamide (3)

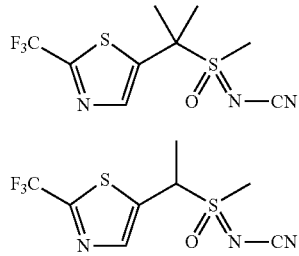

A solution of methyl(oxido){2-(trifluoromethyl)-1,3-thiazol-5-yl]methyl}-λ$^4$-sulfanylidenecyanamide (124 mg, 0.46 mmol) in 8 mL of tetrahydrofuran was cooled to –78° C. under a nitrogen atmosphere and treated with 1.10 mL of a 0.5 M solution of potassium hexamethyldisilazide in toluene and hexamethylphosphroamide (0.04 mL, 0.23 mmol). After 20 minutes, iodomethane (0.3 mL, 4.8 mmol) was added and the mixture allowed to warm to 0° C. over 2 hours. The reaction was quenched with 1M hydrochloric acid and the mixture partitioned between dilute hydrochloric acid and dichloromethane. The organic layer was dried over sodium sulfate and the solvent removed under reduced pressure to yield 180 mg of a yellow syrup. The products and remaining starting material were separated by flash column chromatography on silica gel using a 1% solution of ethanol in dichloromethane. The less polar dimethylated product (50 mg, 39%) was obtained as a pale yellow syrup: 1H NMR (CDCl$_3$) δ 8.05 (s, 1H), 3.05 (s, 3H), 2.08 (s, 6H); LCMS (ESI) m/z 296 (M–H). The diastereomeric mixture of monomethylated products (45 mg, 31%) was obtained as a colorless syrup: 1H NMR (CDCl$_3$) δ 8.03 (d, J=4 Hz, 1H), 5.02 (q, J=8 Hz, 1H), 3.08 (d, J=6 Hz, 3H) 2.05 (d, J=8 Hz, 3H); LCMS (ESI) m/z 282 (M–H).

Example III

1-Oxo-2-(2-trifluoromethyl-thiazol-5-ylmethyl)-tetrahydro-1-λ$^6$-thiophen-1-ylidene-cyanamide

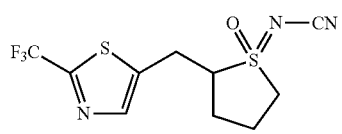

A solution of 1-Oxo-tetrahydro-1-λ$^6'$-thiophen-1-ylidene-cyanamide [prepare in accordance with U.S. patent application 2005228027] (200 mg, 1.39 mmol) in 8 mL of tetrahydrofuran was cooled to –78° C. under a nitrogen atmosphere and treated with 0.60 mL of a 2.5 M solution of n-butyllithium in hexanes. After 15 minutes, 5-(bromomethyl)-2-(trifluoromethyl)-1,3-thiazole (340 mg, 1.39 mmol) dissolved in 1 mL of tetrahydrofuran was added all at once to the mixture. After 90 minutes, the mixture was allowed to warm to –40° C. and quenched with 1M hydrochloric acid. The reaction mixture was partitioned between dilute hydrochloric acid and dichloromethane. The organic layer was dried over sodium sulfate and the solvent removed under reduced pressure to yield 430 mg of a yellow syrup. The mixture was further purified by reverse phase HPLC using an acetonitrile and water mixture as eluant. The diastereomeric mixture of products (71 mg, 17%) was obtained as a pale yellow syrup: 1H NMR (CDCl$_3$) δ 7.90 (s, 1H), 3.4-3.8 (m, 3H), 3.2-3.4 (m, 2H) 1.9-2.7 (m, 4H); LCMS (ESI) m/z 310 (M+H).

Example IV

Methyl(oxido){[2-(trifluoromethyl)-1,3-thiazol-4-yl]methyl}-λ$^4$-sulfanylidenecyanamide (5)

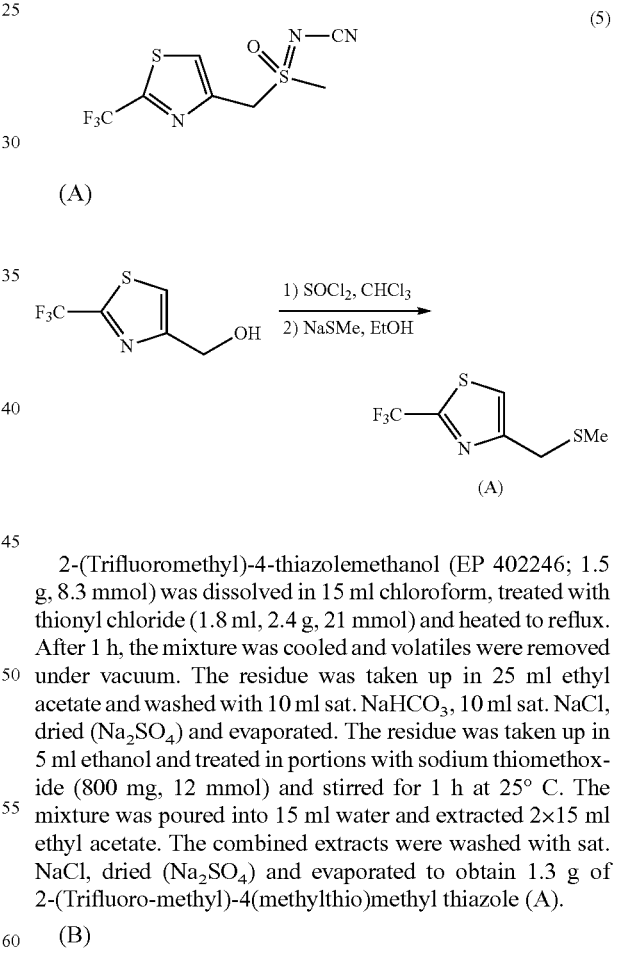

2-(Trifluoromethyl)-4-thiazolemethanol (EP 402246; 1.5 g, 8.3 mmol) was dissolved in 15 ml chloroform, treated with thionyl chloride (1.8 ml, 2.4 g, 21 mmol) and heated to reflux. After 1 h, the mixture was cooled and volatiles were removed under vacuum. The residue was taken up in 25 ml ethyl acetate and washed with 10 ml sat. NaHCO$_3$, 10 ml sat. NaCl, dried (Na$_2$SO$_4$) and evaporated. The residue was taken up in 5 ml ethanol and treated in portions with sodium thiomethoxide (800 mg, 12 mmol) and stirred for 1 h at 25° C. The mixture was poured into 15 ml water and extracted 2×15 ml ethyl acetate. The combined extracts were washed with sat. NaCl, dried (Na$_2$SO$_4$) and evaporated to obtain 1.3 g of 2-(Trifluoro-methyl)-4(methylthio)methyl thiazole (A).

(B)

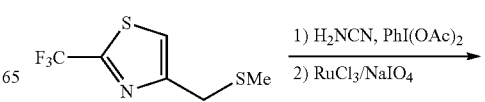

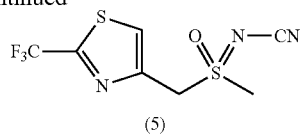

(5)

2-(Trifluoromethyl)-4(methylthio)methyl thiazole (1.3 g, 6.1 mmol) was dissolved in 10 ml dichloromethane, treated with cyanamide (520 mg, 12 mmol), cooled to 0-5° C. and treated with iodobenzene diacetate (2.1 g, 6.7 mmol) in one portion. After 3 h, the solvent was removed by evaporation and the residue was chromatographed on silica eluting with 5% methanol/25% ethyl acetate/70% dichloromethane to give 680 mg of the intermediate sulfilimine. This material was dissolved in 7 ml dichloromethane and poured into a stirred mixture of sodium periodate (1.1 g, 5.4 mmol) and ruthenium trichloride hydrate (30 mg, 0.14 mmol) in 7 ml water. The mixture was stirred for 2 h at 25° C., the dichloromethane phase was separated and the aqueous phase was extracted once with 10 ml dichloromethane. The combined extracts were dried ($Na_2SO_4$), evaporated and the residue was chromatographed on silica eluting with 1% methanol/25% acetone/75% hexane to give 335 mg of methyl(oxido){[2-(trifluoromethyl)-1,3-thiazol-4-yl]methyl}-$\lambda^4$-sulfanylidenecyanamide (5). MP 66-68° C. Electrospray MS M+=246.

Example V

Insecticidal Testing

The compounds identified in the foregoing examples (compounds 1-5) and in Table 1 (compounds 6-18) were tested against cotton aphid using procedures described hereinafter.

Insecticidal Test for Cotton Aphid (*Aphis gossypii*) in Foliar Spray Assay

Squash with fully expanded cotyledon leaves were trimmed to one cotyledon per plant and infested with cotton aphid (wingless adult and nymph) 1 day prior to chemical application. Each plant was examined before chemical application to ensure proper infestation (ca. 30-70 aphids per plant). Compounds (2 mg) were dissolved in 2 ml of acetone:methanol (1:1) solvent, forming stock solutions of 1000 ppm. The stock solutions were diluted 5× with 0.025% Tween 20 in $H_2O$ to obtain the highest test solution at 200 ppm. A lower test concentration (50 ppm) was prepared by making sequential a 4× dilution from the 200 ppm solution with a diluent consisting 80 parts of 0.025% Tween 20 in $H_2O$ and 20 parts of acetone:methanol (1:1). A hand-held Devilbiss sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for 3 days at approximately 23° C. and 40% RH before the number of live aphids on each plant was recorded. Insecticidal activity was measured by Corrected % Control using Abbott's correction formula and the values for the lower test concentrations are presented in Table 1:

Corrected % Control=100*(X−Y)/X where X=No. of live aphids on solvent check plants
Y=No. of live aphids on treated plants

TABLE 1

| Comp # | CA 200 | CA 50 |
|---|---|---|
| 1 | A | A |
| 2 | A | C |
| 3 | A | A |
| 4 | A | A |
| 5 | C | E |

CA 200 refers to % control at 200 ppm against cotton aphid in foliar spray tests, CA 50 refers to % control at 50 ppm against cotton aphid in foliar spray tests,
In each case of Table 2 the rating scale is as follows:

| % Control (or Mortality) | Rating |
|---|---|
| 90-100 | A |
| 80-89 | B |
| 70-79 | C |
| 60-69 | D |
| 50-59 | E |

Insecticide Utility

The compounds of the invention are useful for the control of insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and ticks, and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*

Thysanoptera—*Frankliniella occidentalis*, *Thrips* spp., *Scirtothrips dorsalis*

Isoptera—*Reticulitermes flavipes*, *Coptotermes formosanus*

Orthoptera—*Blattella germanica*, *Blatta orientalis*, *Gryllotalpa* spp.

Diptera—*Liriomyza* spp., *Musca domestica*, *Aedes* spp., *Culex* spp., *Anopheles* spp.

Hymenoptera—*Iridomyrmex humilis*, *Solenopsis* spp., *Monomorium pharaonic*, *Atta* spp., *Pogonomyrmex* spp., *Camponotus* spp.

Siphonaptera—*Ctenophalides* spp., *Pulex irritans*

Acarina—*Tetranychus* spp., *Panonychus* spp., *Eotetranychus carpini*, *Phyllocoptruta oleivora*, *Aculus pelekassi*, *Brevipalpus phoenicis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Nematoda—*Dirofilaria immitis*, *Meloidogyne* spp., *Heterodera* spp., *Hoplolaimus columbus*, *Belonolaimus* spp., *Pratylenchus* spp., *Rotylenchus reniformis*, *Criconemella ornata*, *Ditylenchus* spp., *Aphelenchoides besseyi*, *Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, or those expressing herbicide resistance, such as "Roundup Ready" seed.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides to obtain control of a wider variety of pests and diseases. When used in conjunction with other insecticides or fungicides, the presently claimed compounds can be formulated with the other insecticides or fungicides, tank mixed with the other insecticides or fungicides, or applied sequentially with the other insecticides or fungicides.

Some of the insecticides that can be employed beneficially in combination with the compounds of the present invention include: antibiotic insecticides such as allosamidin and thuringiensin; macrocyclic lactone insecticides such as spinosad, DE-175, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae*, *B. sphaericus*, *B. thuringiensis* subsp. *aizawai*, *B. thuringiensis* subsp. *kurstaki*, *B. thuringiensis* subsp. *tenebrionis*, *Beauveria bassiana*, *Cydia pomonella* granulosis virus, Douglas fir tussock moth NPV, gypsy moth NPV, *Helicoverpa zea* NPV, Indian meal moth granulosis virus, *Metarhizium anisopliae*, *Nosema locustae*, *Paecilomyces fumosoroseus*, *P. lilacinus*, *Photorhabdus luminescens*, *Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

We claim:

1. A compound of the formula (I)

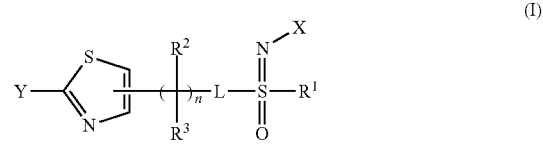

wherein

X represents $NO_2$, CN, $COOR^4$ or $COR^5$;

L represents either a single bond or —$CH(CH_2)_m$— where m is an integer from 1-3 in cases where $R^1$, S and L taken together represent a 4-, 5-, or 6-membered ring;

n is an integer from 0-3;

Y represents fluoro, bromo or iodo;

$R^1$ represents $C_1$-$C_4$ alkyl, $C_1$-$C_4$ haloalkyl, $C_3$-$C_6$ alkenyl, $C_3$-$C_6$ haloalkenyl, $C_3$-$C_6$ alkynyl, or —$(CH_2)$— in cases where $R^1$, S and L taken together represent a 4-, 5-, or 6-membered ring;

$R^2$ and $R^3$ independently represent hydrogen, methyl, ethyl, cyclopropyl, fluoro, chloro, bromo, or iodo;

$R^4$ represents $C_1$-$C_4$ alkyl, $C_1$-$C_4$ haloalkyl, aryl, heteroaryl, arylalkyl or heteroarylalkyl;

$R^5$ represents hydrogen, $C_1$-$C_4$ alkyl, $C_1$-$C_4$ haloalkyl, aryl, heteroaryl; arylalkyl or heteroarylalkyl.

2. A composition for controlling insects which comprises a compound of any claim 1 in combination with a phytologically-acceptable carrier.

3. A method of controlling insects which comprises applying to a locus where control is desired an insect-inactivating amount of a compound of claim 1.

* * * * *